(12) United States Patent
Hernlund et al.

(10) Patent No.: US 12,387,398 B2
(45) Date of Patent: Aug. 12, 2025

(54) SYNCHRONOUS DISPLAY OF QUADRUPED MOTION METRICS

(71) Applicant: SLEIP AI AB, Stockholm (SE)

(72) Inventors: Elin Hernlund, Stockholm (SE); Axel Nyström, Stockholm (SE)

(73) Assignee: SLEIP AI AB, Stockholm (SE)

( * ) Notice: Subject to any disclaimer, the term of this patent is extended or adjusted under 35 U.S.C. 154(b) by 148 days.

(21) Appl. No.: 18/558,263

(22) PCT Filed: May 4, 2022

(86) PCT No.: PCT/EP2022/061997
§ 371 (c)(1),
(2) Date: Oct. 31, 2023

(87) PCT Pub. No.: WO2022/233943
PCT Pub. Date: Nov. 10, 2022

(65) Prior Publication Data
US 2024/0233218 A1     Jul. 11, 2024

(30) Foreign Application Priority Data

May 5, 2021  (SE) .................................. 2150575-5

(51) Int. Cl.
*G06T 11/20*       (2006.01)
*A01K 29/00*       (2006.01)
(Continued)

(52) U.S. Cl.
CPC .......... *G06T 11/206* (2013.01); *A01K 29/005* (2013.01); *A61D 99/00* (2013.01);
(Continued)

(58) Field of Classification Search
None
See application file for complete search history.

(56) References Cited

U.S. PATENT DOCUMENTS

| 2004/0021660 A1* | 2/2004 | Ng-Thow-Hing ... G06V 40/103 345/419 |
| 2016/0073614 A1* | 3/2016 | Lampe ................. A01K 29/005 600/595 |

(Continued)

OTHER PUBLICATIONS

Wang et al., "Identifying lameness in horses through deep learning," Proceedings of the 36th Annual ACM Symposium on Applied Computing, pp. 976-985 (2021).

(Continued)

*Primary Examiner* — Jason A Pringle-Parker
(74) *Attorney, Agent, or Firm* — Fox Rothschild LLP; Carol E. Thorstad-Forsyth

(57) ABSTRACT

A method for displaying quadruped motion metrics, the method comprising obtaining a video capture of a quadruped comprising at least a video segment spanning a gait cycle of the quadruped; extracting, from the video segment, motion data indicative of lameness of the quadruped; processing the motion data extracted from the video segment to generate a motion metric associated with the video segment; generating a dynamic graphical representation of the motion metric for synchronous display with the video segment; synchronously displaying the video segment and the dynamic graphical representation of the motion metric on a display.

20 Claims, 6 Drawing Sheets

(51) Int. Cl.
*A61D 99/00* (2006.01)
*G06V 10/25* (2022.01)
*G06V 20/40* (2022.01)
*G06V 40/20* (2022.01)

(52) U.S. Cl.
CPC .............. *G06V 10/25* (2022.01); *G06V 20/49* (2022.01); *G06V 40/25* (2022.01)

(56) References Cited

U.S. PATENT DOCUMENTS

| | | | | |
|---|---|---|---|---|
| 2017/0262599 | A1* | 9/2017 | Grisel | G16H 30/20 |
| 2019/0244350 | A1* | 8/2019 | Miodini | A61B 5/7267 |
| 2019/0287288 | A1* | 9/2019 | Guay | G06T 13/40 |
| 2019/0298226 | A1* | 10/2019 | Filipowicz | A61B 5/6807 |
| 2021/0059565 | A1* | 3/2021 | Morris | A61B 5/0022 |

OTHER PUBLICATIONS

Wilhelm et al., "FuryExplorer: Visual-Interactive Exploration of Horse Motion Capture Data," Proceedings of Spie, IEEE, US, vol. 9397, 15 pages (2015).
International Search Report and Written Opinion for International PCT Patent Application No. PCT/EP2022/061997 mailed Sep. 9, 2022 (10 pages).
BitRefine group, "Meet BitRefine Heads—multi-purpose deep learning video analysis platform" 5 pages (2019); Available online: <https://bitrefine.group/computer-vision/105-articles/cv-articles/277-deep-learning-video-analysis-platform>.
LucyAnna Westaway (EquiLaterals), "Horse Gait Assessment," YouTube video published on Feb. 6, 2019 and available on and available at the following link: https://www.youtube.com/watch?v=7Oo-GSQ213w.
Mandal, M.K. (2003). Digital Image and Video Processing. In: Multimedia Signals and Systems. The Springer International Series in Engineering and Computer Science, vol. 716. Springer, Boston, MA. (Preview os Chapter 11, 2 pages) Available online: <https://link.springer.com/chapter/10.1007/978-1-4615-0265-4_11 >.
Movavi Vlog, "how to edit *aesthetic* videos? (FULL workflow for beginners) | movavi vlog," YouTube video published on Jun. 28, 2016 and available at the following link: https://www.youtube.com/watch?v=WePNJgS0Rvs&ab_chan•nel=MovaviVlog.
QuinticConsultancy, "Quintic Intelligent Digitisation for Equine Analysis," YouTube video published on Jul. 9, 2019 and available on and available at the following link: https://www.youtube.com/watch?v=2Mmt1dd83Bs.
SimiSystems, "Dog Gait Analysis 2D with Simi Motion," YouTube video published on Oct. 21, 2009 and available at the following link: https://www.youtube.com/watch?v=f1jOrHHC_pU.
SimiSystems, "Dog Gait Analysis in 3D with Simi Motion," YouTube video published on Oct. 14, 2009 and available at the following link: https://www.youtube.com/watch?v=5jbCFLR2olQ.
SimiSystems, "Horse Gait Analysis—Equine biomechanics," YouTube video published on Feb. 23, 2017 and available at the following link: https://www .youtube.com/watch?v=G974Cm3eoMl.
SimiSystems, "Horse Gait Analysis 3D with Simi Motion," YouTube video published on Oct. 19, 2009 and available at the following link: https://www.youtube.com/watch?v=DnZapp8yjRY.
SimiSystems, "Horse Gait Analysis in 2D with Simi Motion," YouTube video published on Oct. 14, 2009 and available at the following link: https://www.youtube.com/watch?v=dvz3ZyUNM0Q&ab.
Yan et al., "Learning the Change for Automatic Image Cropping" 8 pages (2013).

* cited by examiner

SYNCHRONOUS DISPLAY OF QUADRUPED MOTION METRICS

CROSS REFERENCE TO RELATED APPLICATIONS

This application is a U.S. National Phase Application of PCT International Application No. PCT/EP2022/061997, filed on May 4, 2022, which is an International Application of and claims the benefit of priority to Swedish Patent Application No. 2150575-5, filed on May 5, 2021. The entire contents of these Patent Applications are herein incorporated by reference.

TECHNICAL FIELD

The present invention relates to motion data processing and display. More particularly, the present invention relates to the synchronous display of a video segment of a quadruped with motion metrics derived therefrom.

BACKGROUND

Quadrupeds are animals which move on four legs. Examples of quadrupeds include horses, cows, and dogs.

Lameness in quadrupeds may be thought of as a clinically abnormal gait, typically manifesting as an asymmetry (spatial or temporal) or other abnormality in the motion of the quadruped. The causes of lameness vary and these may be progressive. In any event, a timely identification of lameness is key in ensuring the health of the animal.

Traditional techniques for assessing lameness involve an observation of the quadruped in person, typically by a well-trained veterinarian. The gait of the quadruped may not consistently present with lameness, as the animal may respond to stimuli from the environment or exhibit other behaviours that produce movements which may disguise the lameness. Thus, the veterinarian may require a long time observing the animal in order to confidently identify the lameness.

Human vision is also limited in its ability to identify abnormalities in motion, such as asymmetries. It has been consistently demonstrated that human vision can only reliably identify asymmetries of 20% or more, especially at high frequencies (such as when dealing with the moving gait of a quadruped). Thus, a veterinarian may also fail to identify lameness that is not particularly pronounced or progressed.

Some techniques have been developed to aid a trained veterinarian in the identification of lameness. A common class of techniques involves the placement of inertial measurement units (IMUs) on the quadruped and monitoring the output from the IMUs to identify asymmetry with greater sensitivity and accuracy than a human user.

As an alternative to collecting motion data using IMUs, some systems may utilise image capture systems comprising a camera or cameras positioned to capture the gait of the quadruped, e.g. from multiple angles or in binocular arrangements for generating three-dimensional motion data.

SUMMARY OF THE INVENTION

Viewed from a first aspect, there is provided herein a method for displaying quadruped motion metrics, with a view to guiding a human user through the identification of lameness in the quadruped.

The method according to this first aspect comprises obtaining a video capture of a quadruped comprising at least a video segment spanning a gait cycle of the quadruped, and extracting, from the video segment, motion data indicative of lameness of the quadruped. That is, the motion data may be indicative of any lameness that is present, although it is possible that no lameness is present. If the quadruped exhibits lameness, this will affect the motion data in a way that is detectable, even if only detectable by further signal processing means.

The video capture may be obtained by a device implementing the method by any means, such as importing or uploading the video capture to the device. The video capture may be captured by an imaging device separate to or incorporated in the device.

The video capture may contain substantially all of the quadruped within the boundaries of the captured video, throughout the entirety of the captured video or at least a portion thereof, i.e. at least the video segment. The present method may advantageously be able to identify lameness in the quadruped with minimal gait cycles captured in one or more video segments.

As used herein, a 'gait cycle' is the time between contact between one leg and a surface (i.e. a walking or running surface) and the subsequent contact between the same leg and the surface. That is, the motion of the quadruped can be considered as a cyclical (i.e. repeating) motion having a period, phase, magnitude, and the like, akin to a pseudo-sinusoidal signal. Thus, one gait cycle can be thought of as being a period of this motion.

The method according to this first aspect further comprises processing the motion data extracted from the video segment to generate a motion metric associated with the video segment.

This step may be thought of as a signal processing step that abstracts the information in the motion data into a more relevant and useable form for identifying lameness in the quadruped. Furthermore, noise from the motion data may be removed, e.g. through filtering of the motion data, and/or outliers may be removed from the motion data, e.g. by some manual (i.e. user-led) or automatic mathematical means. The outlier removal may preferably be performed under guidance from a user so as to avoid situations whereby mathematical outlier removal inadvertently removes motion data wherein a quadruped's lameness is revealed.

According to some examples, the motion data indicative of lameness comprises symmetry data indicative of a gait symmetry, and the motion metric comprises a symmetry metric. As used herein, "symmetry" refers to spatial or temporal symmetry.

That is, in some examples, extracting motion data comprises determining a motion of at least two positions on the quadruped captured in the video segment as part of the gait cycle, for example constrained in one dimension. For instance, the hips (tubera coxarum) on the rear of a horse may correspond to two positions on a quadruped, and their respective motion as captured in a video segment may correspond to extracted motion data.

To provide a further example, motion data may be extracted from a head, a thoracoabdominal segment and a pelvis of the quadruped. These positions may have, for example, their vertical displacement tracked (i.e. the extracted motion data may be constrained in a vertical dimension). Advantageously, it has been appreciated by the present inventors that the vertical motion symmetry measures of the head and pelvis (e.g. of a horse) are the most stable and clinically relevant metrics for lameness in horses.

Extracting motion data from the video segment may include the use of visual markers on the quadruped during its motion to aid in the extraction of motion data of a position on the quadruped. Alternatively, extracting motion data may comprise not using such markers which, advantageously, would mean that the quadruped did not change or adapt its gait in response to the physical stimulus introduced by the addition of the markers. Moreover, such markerless capture may avoid a problem relating to skin displacement over bony areas of the quadruped that are desired for tracking.

The method according to this first aspect further comprises generating a dynamic graphical representation of the motion metric for synchronous display with the video segment, and synchronously displaying the video segment and the dynamic graphical representation of the motion metric on a display.

For example, the motion metric may be generated for portions of the motion data corresponding to respective portions of the video segment, e.g. for every frame, every 5 frames, every 0.1 second, or some other subdivision of the video segment, or a gait cycle or a portion thereof. Then, synchronously displaying the video segment and the dynamic graphical representation of the motion metric may comprise displaying a graphical representation of the motion metric corresponding to a portion of the video segment at a same time as displaying said portion of the video segment. That is, the dynamic graphical representation may be formed of a sequence of graphical representations played in series. The timing of this sequence may then be synchronised with the display of the video segment, such that a portion of a video segment (e.g. 5 frames) is played at a same time as the graphical representation of the motion metric that was derived from motion data extracted therefrom (i.e., extracted from said 5 frames and processed to generate the motion metric).

In this manner, synchronous display of the dynamic graphical representation and the video segment can be maintained throughout the video segment. The length of these portions can be adjusted according to the desired resolution or frame rate of the dynamic graphical representation. Furthermore, the motion metric may be generated for points between the portions and/or extending before or after the video segment, using interpolation or extrapolation methods.

As used herein, "dynamic graphical representation" refers to a representation of a metric, such as a graph, diagram, animation, or other representation of information that changes with time, e.g. in the form of a time series of 'static' graphical representations.

In some examples, the dynamic graphical representation of the motion metric may be displayed as an overlay over the displayed video capture. Thus, the user can see all of the displayed information (video segment and the graphical representation of the motion metric) without needing to move their eye around the display. This allows for a better understanding of the displayed information. Furthermore, it may be clearer to the user which motion metric is associated with which part of the quadruped.

To present a particular example, motion data may be extracted from a head of the quadruped and a motion metric (e.g. maximum and minimum height during a particular gait cycle) may be generated therefrom. Thereafter, a graphical representation of the motion metric (such as a vertical line extending from said minimum to said maximum height) may be displayed as an overlay over the head of the quadruped. For example, the position information for particular pixels from which the motion data has been extracted may be recorded and the position of the overlay be based at least in part on this position information.

In some examples, the dynamic graphical representation of the motion metric may be displayed at a side of the displayed video segment, such as to the left of the video displayed segment, or below. Displaying the dynamic graphical representation of the motion metric in this way may advantageously prevent the video segment from being unnecessarily obscured, so that the user may clearly see the motion of the quadruped in the video segment.

According to some examples, the method may further comprise cropping the video segment to a region of interest, wherein the region of interest comprises at least a portion of the quadruped, for example the rear of a horse. In these examples, the extracted motion data may be associated with said portion of the quadruped, i.e. if the video segment is cropped to include only the rear of a horse, the extracted motion data would relate only to the motion that is visible from the captured angle of the rear of the horse.

The cropping may be automatically or manually performed. In some examples, the video capture may occur some distance from the quadruped such that it is difficult for a user to see the quadruped clearly in the displayed video segment. In such examples, the cropping may exclude spatial portions of the captured video that do not include the quadruped, thus allowing the user to assess the motion of the quadruped in greater detail.

In some examples, obtaining a video capture of the quadruped may comprise obtaining a plurality of video captures of the quadruped, each containing respective video segments spanning at least the gait cycle. For example, the plurality of video captures may each be captured by a respective image capture device, which may be arranged to capture different angles of the quadruped. Such an arrangement may advantageously allow for motion data to be viably extractable from at least one of the video captures, as the quadruped moves around a space or faces different directions.

According to such examples, synchronously displaying the video segment and the dynamic graphical representation of the motion metric on the display may then comprise selecting a video segment from the plurality of video captures for synchronous display with the dynamic graphical representation of the motion metric. The video segment that most representatively captures the motion of the quadruped may be selected, by manual or automatic means.

Each of these video captures may only capture a single gait cycle of the quadruped. This may be the same gait cycle or different gait cycles for each video capture. In the case where multiple image capture devices, having different fields of view, capture the same gait cycle, depth information may advantageously be derived therefrom.

In some examples, the video capture spans more than one gait cycle, such as 1.5 gait cycles, 5 gait cycles, 20 gait cycles, or more, or less, but still more than only one. In such cases, extracting motion data from the video segment comprises segmenting the video capture into at least the video segment spanning the gait cycle. This segmentation advantageously allows for a single gait cycle (for example, a gait cycle deemed to be of particular interest by a user) to be played on loop whilst the associated dynamic graphical representation is displayed synchronously. Furthermore, this segmentation may be performed before substantive extraction of the motion data from the portions (e.g. frames) of the video segment. Thus, if only data from a single gait cycle is required, the amount of image processing resources consumed may be reduced by trimming the video capture into a segment containing the relevant captured gait cycle.

This segmentation may be performed by any means. For example, segmenting the video capture may comprise identifying, from the motion data, a first point in the gait cycle, identifying, from the motion data, a second point in a subsequent gait cycle, said second point corresponding to said first point, and segmenting the video capture into a video segment from the first point to the second point. The second point may correspond to the first point in the sense that these points are taken at the same time during a gait cycle (e.g. at a start of respective gait cycles, or half-way through a gait cycle etc.). These points may be identified in the motion data by, for example, identifying a lowest vertical displacement of a position on the quadruped (such as the head of the quadruped). As another example, one of the feet of the quadruped may be tracked, or one of the legs.

In some examples, the motion data used to identify the segmentation points may be the same motion data that is processed to generate the motion metric; thus the amount of data extracted from the video segment is further reduced. Alternatively, the motion data in which the first and second points are identified may be a different type of motion data used only for segmentation (e.g. the vertical motion of the head of a quadruped).

In some cases, multiple (i.e., two or more) gait cycles may be captured in the video capture, and the video capture may be segmented into individual gait cycles. That is, in some examples, the video capture may span a plurality of gait cycles, and segmenting the video capture comprises segmenting the video capture into multiple video segments, each video segment spanning a respective gait cycle of the quadruped. Thereafter, the user may choose to review each of these gait cycles (and their associated motion metrics).

Additionally or alternatively, extracting motion data from the video segment may comprise selecting the video segment from the multiple video segments of the video capture. That is, the user may be prompted to select a gait cycle that is most likely to indicate lameness, for further processing and review. This advantageously limits the data processing to focus on a video segment that is most likely to be useful for identifying lameness in the quadruped.

Motion metrics may additionally be generated for every gait cycle that is captured in a video capture, and the video capture (or captures) may be broken into segments and each video segment may have a generated motion metric associated therewith and a dynamic graphical representation of the motion metric generated therefor.

For example, extracting motion data from the video segment may comprise extracting respective sets of motion data for each video segment of the multiple video segments; generating the motion metric may comprise generating the motion metric for each set of motion data; generating a dynamic graphical representation may comprise generating a respective dynamic graphical representation associated with each video segment; and said synchronous displaying may comprise displaying each video segment synchronously with the associated dynamic graphical representation.

The multiple video segments may comprise consecutive video segments from a same video capture, or the multiple video segments may be from distinct portions of a video capture, and/or the video segments may be captured as part of different video captures, e.g. by different imaging devices.

When processing motion data extracted from multiple video segments, each showing a different gait cycle of the quadruped, it may be helpful to a user in identifying lameness in the quadruped to show a sequence of successive gait cycles (them having happened consecutively or merely being displayed as such). In this way, a user may be able to easily identify temporal asymmetries in the gait of the quadruped. For example, it may become apparent when viewing multiple gait cycles and their associated motion metrics, displayed in a dynamic graphical representation thereof, that the quadruped changes its gait from gait cycle to gait cycle. This may be a strong indicator of lameness of a quadruped.

In order to make this temporal asymmetry more apparent to the user, at least a portion of the dynamic graphical representation may be persisted on the display after displaying the video segment. For example, synchronously displaying the video segment with the dynamic graphical representation may comprise displaying a dynamic graphical representation associated with a different video segment in addition to the dynamic graphical representation associated with the video segment. Thus, the dynamic graphical representations for two or more gait cycles may be directly graphically compared. This makes it even easier for a user to identify even very subtle lameness, as characterised by such temporal asymmetries in the gait of the quadruped.

The dynamic graphical representation associated with the different video segment may be graphically represented different to the dynamic graphical representation associated with the video segment, such as reduced in opacity, made a different colour, or the like. Thus, the user may be able to clearly identify which represented motion metric is associated with the currently displayed video segment.

It is also possible that at least a portion of a dynamic graphical representation associated with a future video segment (i.e. a video segment yet to be displayed to the user) is displayed at a same time as that associated with the currently displayed video segment. Thus, the motion of the quadruped across both past and future gait cycles may be compared to the gait cycle currently under review at any given time. This may further improve the assessment of temporal asymmetry of the motion of the quadruped.

In some examples, the method according to the first aspect may include capturing the video capture using an imaging device (an RBG camera, infrared camera, high-speed camera, stereo camera arrangement, or other image capture device or arrangement).

According to these examples where the video capture is captured using an imaging device, at least a portion of: the extracting of the motion data, the processing of the motion data, the generating of the dynamic graphical representation, or the synchronous displaying of the video segment and the dynamic graphical representation of the motion metric, may be performed contemporaneously with said capturing of the video capture. That is, the method may be performed in 'real-time', such that a near-live image capture can be processed and motion metrics generated therefor. For example, a video stream may be captured live, and a dynamic graphical representation may be generated in a near-live fashion so as to provide, for example, an overlay on the live (or near-live) video capture. For example, the method may be implemented as part of augmented reality (AR) or virtual reality (VR) systems.

According to a second aspect of the invention, there is provided a device comprising a display and one or more processors adapted to execute the steps of the method disclosed herein. The device may comprise an imaging device adapted to capture the video capture. That is, the imaging device may form part of the same device that comprises the display on which the video segment and the dynamic graphical representation are displayed. For example, the device may be a mobile telephone having a camera and a screen, a tablet device, a wearable device, or other such suitable device.

According to other aspects of the invention, there is provided a computer program comprising instructions to cause such a device to implemented the disclosed method, and a computer-readable medium having stored therein the computer program. The computer readable medium may be any suitable medium for the storage and/or transfer of data to or from a computer, such as a wave medium, a hard-disk drive (HDD), a solid-state drive (SSD), read-only memory (ROM) or other such transitory or non-transitory computer readable media, or storage media.

According to the aspects of the present invention, the advantages of computer aided techniques may be better leveraged through guiding a human user, rather than attempting to identify lameness using computer means in isolation.

For examples, IMU systems may be limited in their ability to accurately and quickly identify lameness in a quadruped due to their reliance on sensors that physically contact the quadruped. The quadruped may alter its motion in response to such physical stimuli and, thus, abnormality in the motion of the quadruped may not reliably be attributed to lameness, or the quadruped may be minded to consciously alter its gait to account for the physical stimuli and thus its lameness may not present at all.

Computer vision systems (image capture systems) may address some of these limitations, but they too are limited in their ability to actually identify lameness in the quadruped. This is due at least in part to the fact that human users of such systems cannot easily relate the often noisy motion data to the motion of the horse.

Indeed, computer vision systems may implement mathematical processing means that exclude outliers in collected data. However, these outliers may well be a result of the quadruped presenting with its lameness. Thus, as users are unable to properly relate the data output from such systems to the actual motion of the horse from which the data have been generated, lameness may not be quickly or accurately identified.

Thus, by processing raw motion data extracted from a video segment into a motion metric, generating a dynamic graphical representation of said motion metric, and then synchronously displaying said dynamic graphical representation with the video segment that it was derived from, a user can readily relate processed motion data to the actual motion of the quadruped.

As such, the user may be able to identify, from viewing a video capture, which gait cycles spanned by the video capture are of particular interest because it will be easier to identify when the quadruped is presenting its 'true' gait and thus when its lameness, if any, is most likely to manifest in the motion data.

It is also possible that the quadruped may exhibit strange behaviours due to external stimuli such as sounds or other animals, and a user witnessing the motion data resulting from this behaviour may falsely conclude that the quadruped is exhibiting lameness. However, such strange behaviours would be easily recognisable in the synchronously displayed video segment and thus the portion of the dynamic graphical representation generated for such a video segment spanning such strange behaviour, if generated, may be readily dismissed. Alternatively, the video segment spanning a period of strange behaviour may be ignored at the outset such that motion data is not extracted therefrom, thus reducing the resources consumed in processing irrelevant motion data.

Coupled with the ability of computer vision systems to exaggerate otherwise imperceivable motions (i.e. otherwise imperceivable to the human eye), the present system may thus enable the identification of even very subtle lameness in the quadruped with a minimum of data collection.

Hence, the present invention allows for a quicker and more accurate identification of lameness in quadrupeds when compared to existing techniques.

In some examples, the quadruped is referred to as being a horse. However, it will be appreciated that the disclosed methods may be applied to any quadruped whose lameness manifests as an abnormality in gait.

BRIEF DESCRIPTION OF THE DRAWINGS

One or more embodiments will be described, by way of example only, and with reference to the following figures, in which.

Figure 1:
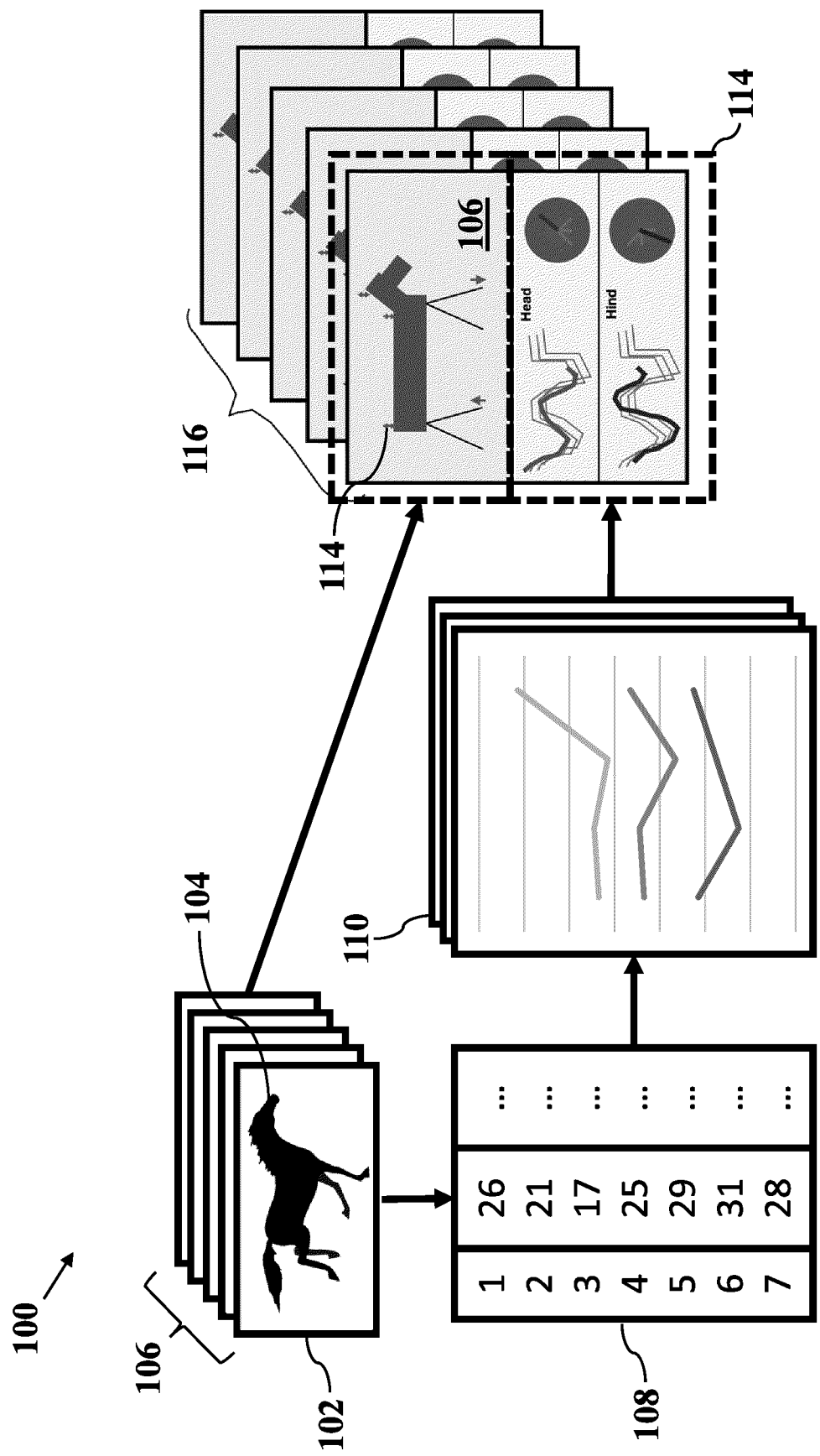
FIG. 1 schematically shows a process for displaying motion metrics of a quadruped, according to an embodiment of the invention.

Whilst the invention is susceptible to various modifications and alternative forms, specific embodiments are shown by way of example in the drawings are herein described in detail. It should be understood, however, that the detailed description herein and the drawings attached hereto are not intended to limit the invention to the particular form disclosed. Rather, the intention is to cover all modifications, equivalents, and alternatives falling within the scope of the appended claims.

Any reference to prior art documents or comparative examples in this specification is not to be considered an admission that such prior art is widely known or forms part of the common general knowledge in the field.

As used in this specification, the words "comprise", "comprising", and similar words are not to be interpreted in the exclusive or exhaustive sense. In other words, they are intended to mean "including, but not limited to".

DETAILED DESCRIPTION

The present invention is described in the following by way of a number of illustrative examples. It will be appreciated that these examples are provided for illustration and explanation only and are not intended to be limiting on the scope of the present invention. Instead, the scope of the present invention is to be defined by the appended claims. Furthermore, although the examples may be presented in the form of individual embodiments, it will be recognised that the invention also covers combinations of the embodiments described herein.

FIG. 1 schematically shows a process 100 for displaying motion metrics of a quadruped, according to an embodiment of the invention.

As shown in FIG. 1, the process includes obtaining a video capture 102 of a quadruped 104, the video capture 102 comprising at least a video segment 106 spanning a gait cycle of the quadruped 104.

In the example illustrated in FIG. 1, the video capture 102 consists entirely of the video segment 106, and spans, for example, one gait cycle of the quadruped 104. That is, as schematically shown, the video capture 102 may comprise a plurality of portions, such as frames, fractions of a second (one tenth, one quarter, etc.) or some other subdivision of time that, collectively, span a gait cycle of the quadruped 104. As shown, the quadruped 104 in this example is a horse. For the purposes of illustration only, the portions of the video capture 102 shall be referred to as frames of the video capture 102 for the remainder of the discussion of FIG. 1.

The video capture 102 and/or the video segment 106 may be cropped to a region of interest containing at least a portion of the quadruped 104. In the illustrated example, the region of interest incorporates the entirety of the quadruped 104.

The process 100 shown in FIG. 1 further comprises extracting, from the video segment 106, motion data 108 indicative of lameness of the quadruped 104. In the example shown, the motion data 108 is numerical data in column format, although it will be appreciated that the motion data 108 may be stored in any suitable form for processing.

The extracted motion data 108 may include, for example, a location (absolute or relative) of a position on the quadruped 104. For example, the motion data 108 may include the location of a left front leg of the quadruped 104 relative to a right front leg. Additionally or alternatively, the motion data may comprise a location of the head of the quadruped 104 in a vertical direction. The extracted motion data 108 may be taken frame to frame on a relative basis, i.e. indicated the motion of the position on the quadruped relative to the previous frame of the video segment 106.

In some examples, the motion data 108 may be symmetry data, and extracting the motion data 108 may comprise determining a motion of at least two positions on the quadruped 104 captured in the video segment 106 as part of the gait cycle. The two positions may be the height of the hips of a horse, i.e. constrained in one dimension, or the two positions may be a hoof of a horse and a head of the horse, or the two positions may be a leg and a head of a dog, to name a few examples.

Taking a particular example of monitoring the height of the hips of a horse, the motion data 108 may be symmetry data extracted from the video segment 106 and the symmetry data by be a relative vertical motion of each hip of a horse. A horse exhibiting lameness would, for example, present with an asymmetrical motion between a right and a left hip (e.g., a left hip being higher than the right hip during the gait cycle).

To take another example, the at least two positions that are tracked for motion extraction may comprise a head, a thoracoabdominal segment and a pelvis of the quadruped. These positions may have, for example, their vertical displacement tracked (i.e. the extracted motion data may be constrained in a vertical dimension).

If the video capture 102 (or video segment 106 if these are not one and the same) has been cropped to a region of interest, the extracted motion data 100 may relate only to this region of interest (e.g. the head of a horse).

As indicated by arrow from the motion data 108, the motion data 108 extracted from the video segment 106 is processed to generate a motion metric 110 associated with the video segment 106. The motion metric 110 is illustrated as being a graphic but the motion metric 110 may also be numerical, textual, a colour, or some other abstracted form of information. That is, extracted motion data 108 may be thought of as a raw signal taken from the video segment 102 and the motion metric 110 may be thought of as having undergone a signal processing step that abstracts the information into a more relevant and useable form for identifying lameness in the quadruped 102.

Examples of a motion metric 110 generated according to the illustrated process 100 may be a maximum and/or minimum height of a position on the quadruped 104, a time to complete a gait cycle, a relative timing between legs of the quadruped 104 (either directly measured from the video segment 106 or inferred from other positions on the quadruped 104, e.g. the hips, shoulders, and/or head, etc.), or the like. The motion metric 110 may exaggerate otherwise imperceivable motions of the quadruped captured in the motion data 108.

There may be one value of the motion metric 110 generated per portion (e.g. per frame) of the video segment 106. Alternatively, there may be one value of the motion (or symmetry) metric 110 generated for the entire video segment 106, or per gait cycle or portion thereof, depending on the nature of the generated motion metric 110.

In some examples, not all of the motion data 108 will be included in the generation of the motion metric 110, for example, some may contribute instead to the segmenting of the video capture 102, as discussed in more detail below.

The illustrated process 100 terminates with the generation of an image stream 116 for a display. The image stream 116 comprises a synchronous display of the video segment 106 and a dynamic graphical representation 114 of the motion metric 110. The generation of the image stream 116 for the display includes generating the dynamic graphical representation 114 of the motion metric for synchronous display with the video segment 102. This may include animating a motion metric 110 for correspondence with the associated video segment 106, or a generation of a graphic representation for each frame of the video segment 106 so that each frame of the image stream 116 comprises a frame of the video segment 106 and a corresponding graphical representation of a motion metric 110 associated therewith. Thus, the motion of the quadruped may be displayed with a representation of motion metrics 110 derived therefrom, and displayed in a way that assists the user in making sense of the motion of the quadruped.

It will be appreciated by those skilled in the art that a motion metric 110 may require, for example, two pieces of motion 108 to generate and, thus, there may be one generated motion metric 110 (or one value thereof) for every two frames of the video segment 106. In such cases, the image stream 116 may synchronously display a graphical representation of said motion metric 110 at a same time as said corresponding two frames of the video segment. As an alternative, the motion metric 110 may be interpolated between neighbouring values so as to generate a smooth motion and/or an increased frame rate for the dynamic graphical representation 114, thus improving the user perception of the motion metric 110.

As can be seen in the upper portion of the image stream 116, the video segment 106 may have overlaid thereon a further dynamic graphical representation 114 of a motion metric 110, e.g. an arrow associated with a portion of the quadruped 104 to graphically represent a motion metric 110 associated with said portion of the quadruped 104 (e.g. a range of vertical or horizontal motion during a gait cycle).

The dynamic graphical representation 114 and the video segment 106 are synchronously displayed in the sense that each generated image of the image stream 116 contains a graphical representation of a motion metric 110 that has been generated for the portion (e.g. frame) of the video segment 106 shown in said image. Therefore, a user can easily interpret the motion of the quadruped 104 shown in the video segment 106 during a gait cycle and may thus easily identify lameness in the quadruped 104.

The image stream 116 may be a loop of a gait cycle of the quadruped 104. Alternatively, the image stream 116 may contain multiple gait cycles of quadruped 104 captured in one or more video segments 106, each having dynamic graphical representations 114 associated therewith for synchronous display therewith.

Figure 2:
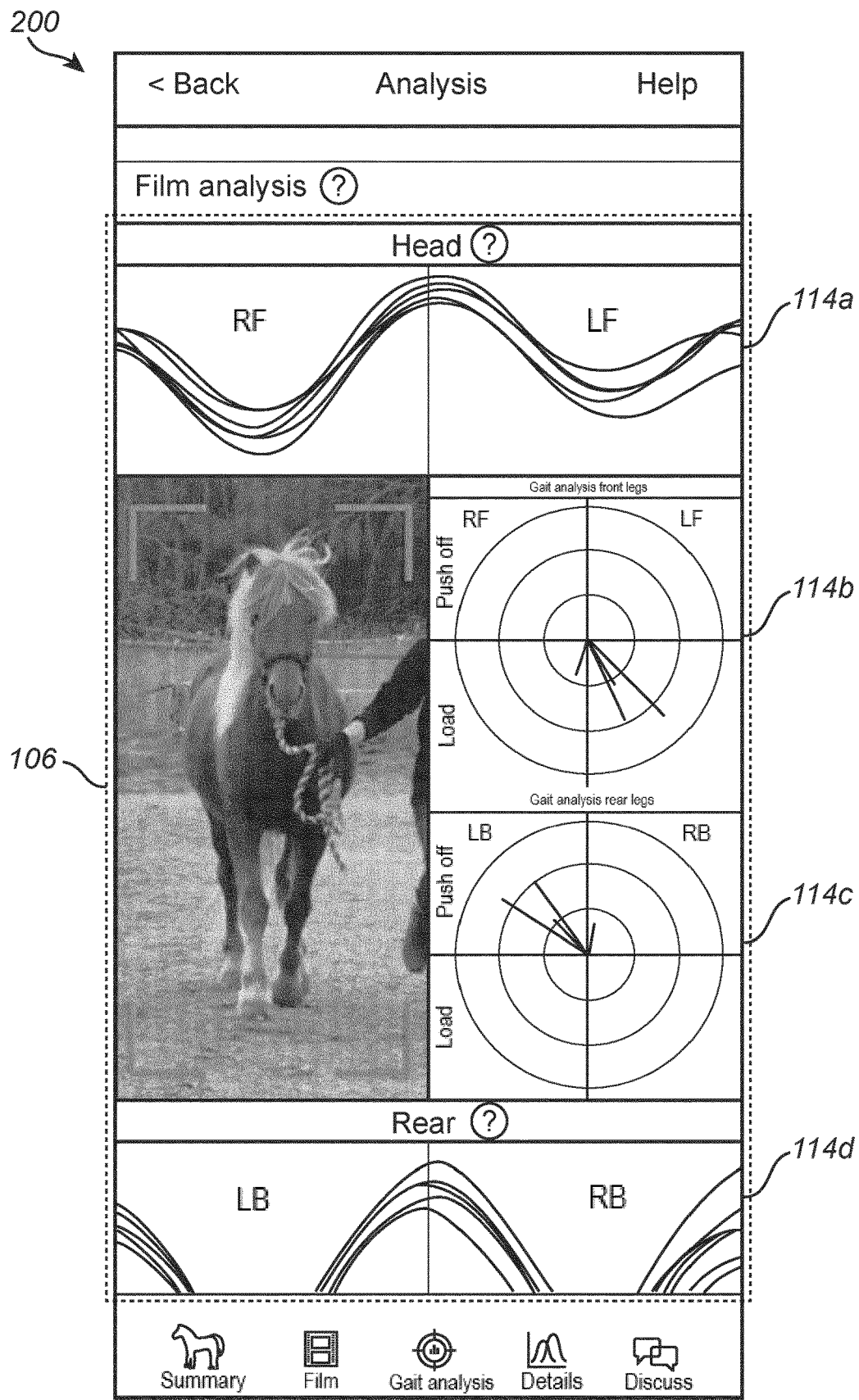
FIG. 2 shows a display having a video segment and a dynamic graphical representation of motion metrics, according to an example implementation.

FIG. 2 shows a display 200 having a video segment and 102 dynamic graphical representations 114*a*-114*d* of motion metrics, according to an example implementation.

In the illustrated example, the video segment 106 shows a front view of a horse. The video segment 106 may have been segmented from a video capture that contained more than one gait cycle, and the video segment 106 may have been segmented therefrom so that the video segment 106 spans a gait cycle of the horse.

The display 200 comprises a four different dynamical graphical representations of motion metrics generated from the video segment of the horse (i.e. the metrics have been generated from motion data extracted at least from the displayed video segment 106).

Dynamic graphical representation 114*a* is a pseudo-sinusoidal graphical representation of the vertical motion of the front portions of the horse. That is, during the gait cycle, the horse's front may typically move in a pseudo-sinusoidal manner, varying between right and left (HF and VF). The dynamic graphical representation 114*a* may be separated into portions representing different portions of the horse (e.g. right and left) so as to further assist a user in identifying any abnormalities in the motion of the horse, e.g. asymmetry between the left motion and the right motion of the front of the horse. In some examples, a motion of the head may be tracked throughout a gait cycle and the lowest points may be monitored for. Each lowest point thus corresponds to a half of a gait cycle and can be attributed to the motion of one side (e.g. left or right leg) of the quadruped.

Dynamic graphical representation 114*b* shows a dynamic graphical representation of an estimated load on respective front feet of the quadruped. The estimated load may be derived from a motion of the feet themselves or inferred from a motion of another position of the quadruped, such as its shoulders or head.

The dynamic graphical representation takes the form of a line that indicates a motion symmetry between the left and right feet of the quadruped, and their relative load. Such data can be indicative of lameness, as a quadruped may place less load onto a leg that is lame.

Dynamic graphical representation 114*c* is similar to dynamic graphical representation 114*b*, except it has been generated in relation to the rear of the horse.

Dynamic graphical representation 114*d* is similar to dynamic graphical representation 114*a*, except it has been generated in relation to the rear of the horse.

As can be seen, for example, in dynamic graphical representations 114*a* and 114*d*, there are multiple dynamic graphical representations shown in the same view, in this case overlaid on one another, with some faded relative to a primary (i.e. darkest coloured) dynamic graphical representation. These faded lines may correspond to dynamic graphical representations that are associated with different gait cycles than that currently displayed in the video segment 106. In the illustrated, these are persisted in their entirety (i.e. the other, e.g. previously generated, dynamic graphical representations are kept static across their entire scope).

The current dynamic graphical representation (i.e. the current pseudo-sinusoidal wave having a darker colour) is overlaid with these previous waves having a lighter colour in a synchronous manner with corresponding portions of the video segment 106. That is, the 'drawing' of the darker coloured waveform will be timed in such a way that the represented motion metric corresponds to that generated from motion data extracted from the currently displayed portions of the video segment. The user may thus observe the motion of the horse synchronously with the dynamic graphical representation of motion metrics generated from the video segment showing the horse.

In some examples, the multiple displayed graphical representations may have been derived from consecutive video segments from a same video capture. Alternatively, these may have been derived from a select subset of video segments, e.g. from different video captures, that best represent the 'true' motion of the horse, as determined automatically through signal processing, statistical distribution analysis, machine learning means or through a selection of a user.

The simultaneous display of multiple graphical representations from different gait cycles allows for a user to compare the motion of the quadruped across gait cycles. Thus, the temporal asymmetry of the gait of the quadruped may be accurately assessed by the user.

Figure 3:
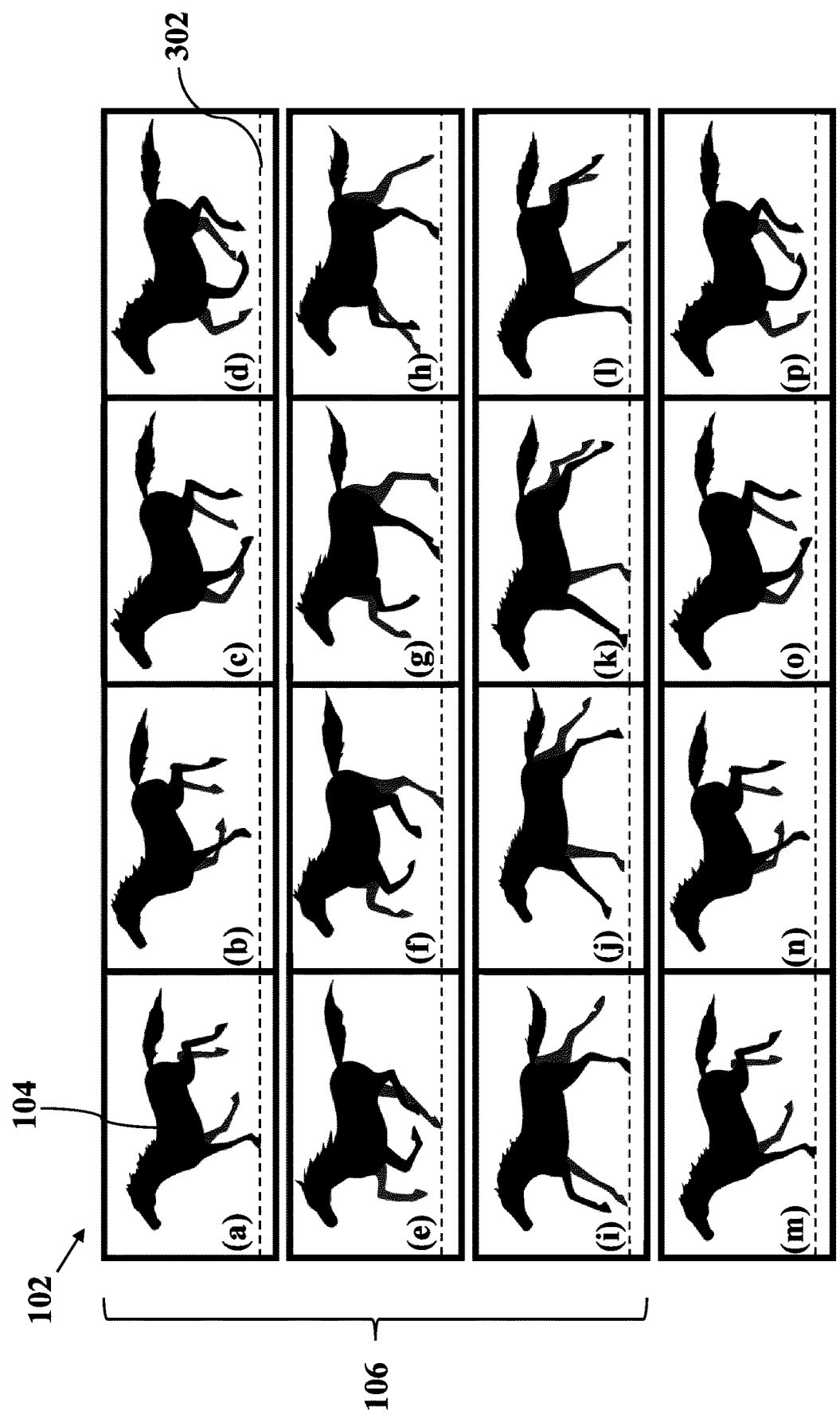
FIG. 3 schematically shows a video capture of a quadruped spanning more than one gait cycle, according to an example implementation.

FIG. 3 schematically shows a video capture 102 of a quadruped 104 spanning more than one gait cycle, according to an example implementation.

The video capture 102 has been illustrated as a series of portions (a)-(p) representing, for example, frames of video capture 102. The video capture 102 may have been cropped to centre around the quadruped 104.

According to some examples, the video capture 102 may be trimmed or segmented into at least a video segment 106. Motion data extracted from the video capture 102 may be used said segmenting. For example, segmenting the video capture may involve identifying, from the motion data, a first point in the gait cycle. That is, a first point in time may be arbitrarily selected or selected according to a rule (e.g. minimum vertical position of a forward-most location of the quadruped, or the contact of a particular foot with a surface 302). It is noted that every point during the walking or running motion of a quadruped 104 is 'in the gait cycle' in this sense, due to the cyclical nature of the gait cycle. Thus, the first point may be thought of as a phase value during the cycle, e.g. arbitrarily defining that the first point corresponds to a phase of zero. For the purposes of illustration, frame (a) of the video capture may be identified as a first point in the gait cycle.

Segmenting the video capture 102 may then involve identifying, from the motion data, a second point in a subsequent gait cycle, said second point corresponding to said first point. The second point corresponds to the first point in the sense that it will have the same phase value during a subsequent gait cycle, i.e. the quadruped 104 has completed a whole number of gait cycles (e.g. one) between the first point and the second point. The motion data for the second point may take a same value as that for the first point or similar thereto, in some examples.

In the presently illustrated example, frame (m) may be identified as the beginning of a new gait cycle because frame (m) corresponds to the subsequent instance of the forward-left foot of the quadruped 104 contacting the surface 302.

The video capture 102 may therefore be cut between frames (1) and (m) to segment the video capture into a video segment 106 from frame (a) to frame (m) (not including frame (m)) that spans one gait cycle. Frames (m) to (p) may be preserved or they may be discarded to reduce the amount of motion data processed into motion metrics.

Figure 4:
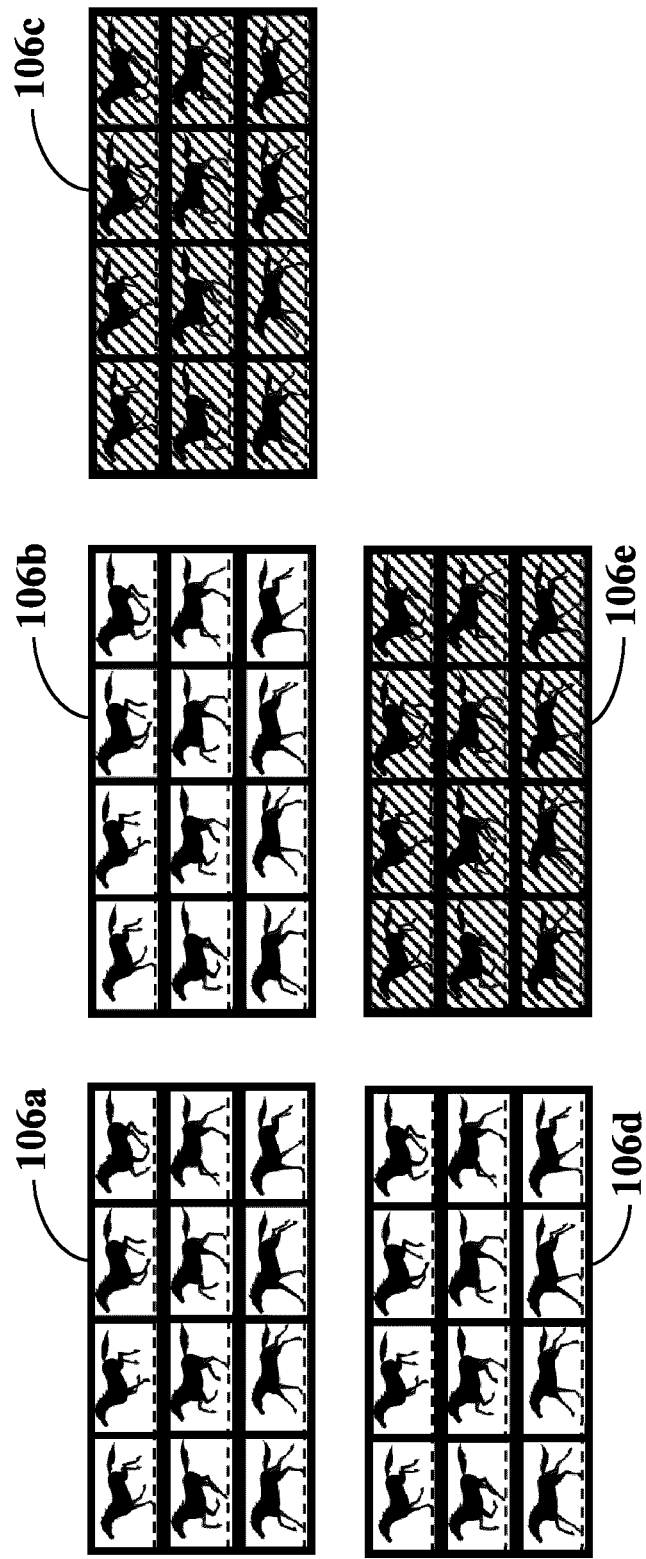
FIG. 4 schematically shows multiple video segments of a video capture of a quadruped, according to an example implementation.

FIG. 4 schematically shows multiple video segments 106a-106e of a quadruped, according to an example implementation.

The video segments (collectively referred to as 106) may have been segmented from one or more video captures by a process similar to that described in relation to FIG. 3.

A user may be prompted to review the multiple video segments 106, each spanning a respective gait cycle of the quadruped, in order to select one or more video segments for further review, e.g. for generating a motion metric therefrom and for synchronously displaying said video segments with a dynamic graphical representation of the motion metric.

In the presently illustrated example, the user may select video segments 106a and 106b (which are consecutive video segments of a same video capture) and 106d (which has been taken from a different video capture) for use in identifying lameness of the quadruped. Thereafter, video segments 106c and 106e may be discarded.

Video segments 106a and 106d may have been captured simultaneously and may therefore show a same gait cycle of the quadruped, e.g. from different camera angles. Thus, when synchronously displaying a video segment with a dynamic graphical representation of motion metrics, one of the video segments 106a and 106d may be selected for said synchronous display. For example, segment 106a may be selected. Nevertheless, at least some of the motion data extracted from video segment 106d may still be used in generating the motion metric. In this way, synchronous display of the video segment 106a is achieved with more accurate motion metrics represented in the dynamic graphical representation because the motion metric has been generated from multiple sets of motion data pertaining to a same gait cycle.

In some examples, the video segments 106 may be selected or deselected by machine learning means, e.g. identifying video segments 106 that do not properly capture the quadruped, or capture motion of the quadruped that is irrelevant for lameness assessment, and/or capture the quadruped when it is not moving, for example, and discarding of these.

Figure 5:
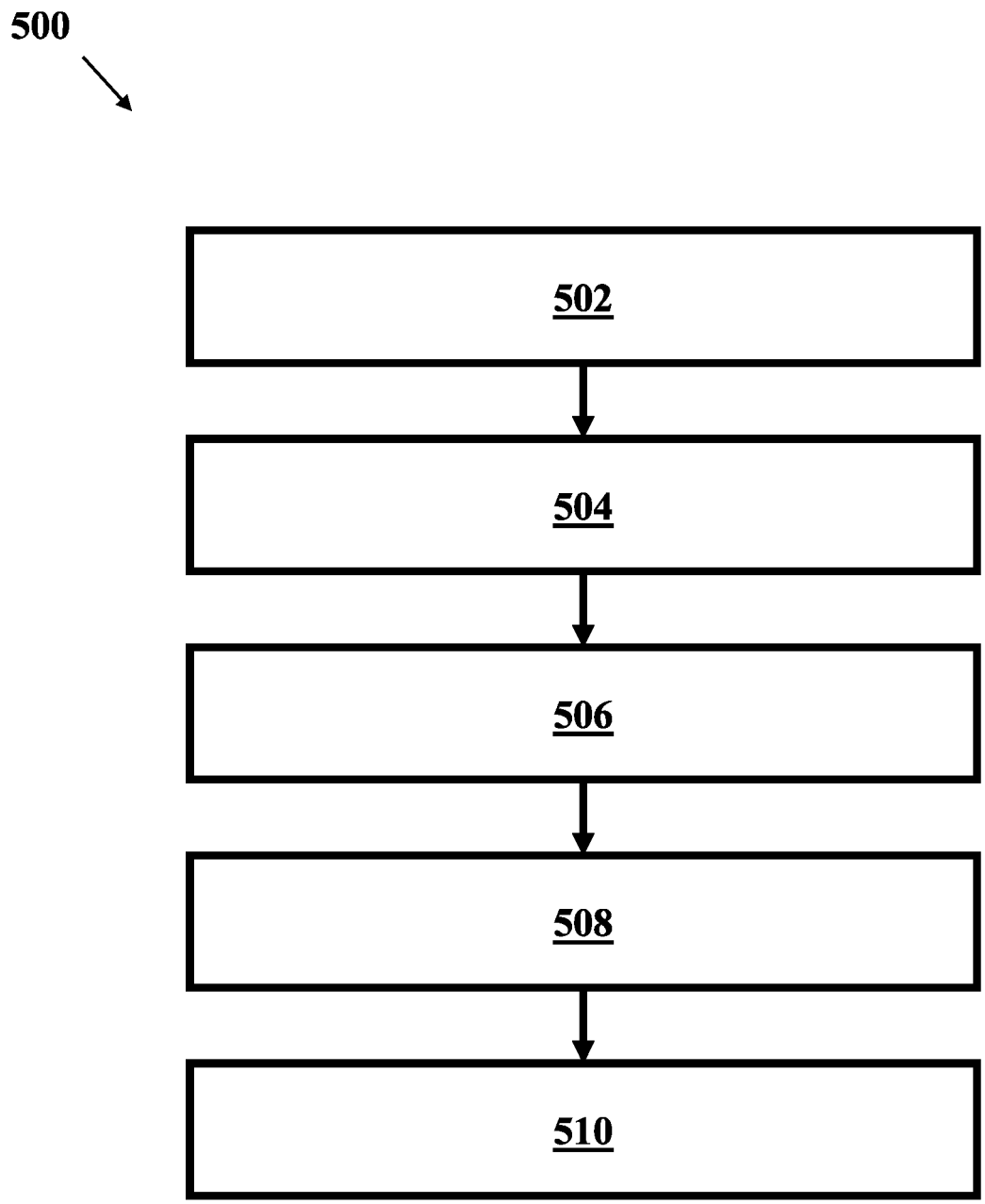
FIG. 5 schematically shows a method for displaying motion metrics of a quadruped, according to an embodiment of the invention.

FIG. 5 schematically shows a method 500 for displaying motion metrics of a quadruped, according to an embodiment of the invention.

As indicated by the block 502, the method 500 comprises obtaining a video capture of a quadruped comprising at least a video segment spanning a gait cycle of the quadruped.

Thereafter, as indicated by the block 504, the method 500 further comprises extracting, from the video segment, motion data indicative of lameness of the quadruped.

Once the motion data has been extracted, or at least partially during said extraction, the method 500 may further comprise processing the motion data extracted from the video segment to generate a motion metric associated with the video segment, as indicated by block 506.

Then, as indicated by block 508, the method 500 further comprises generating a dynamic graphical representation of the motion metric for synchronous display with the video segment.

Finally, and as indicated by block 510, the method 500 further comprises synchronously displaying the video segment and the dynamic graphical representation of the motion metric on a display.

Although the method steps have been illustrated and discussed as being sequential, it will be appreciated that at least some of these steps 502-510 may be carried out simultaneously or at least contemporaneously.

Figure 6:
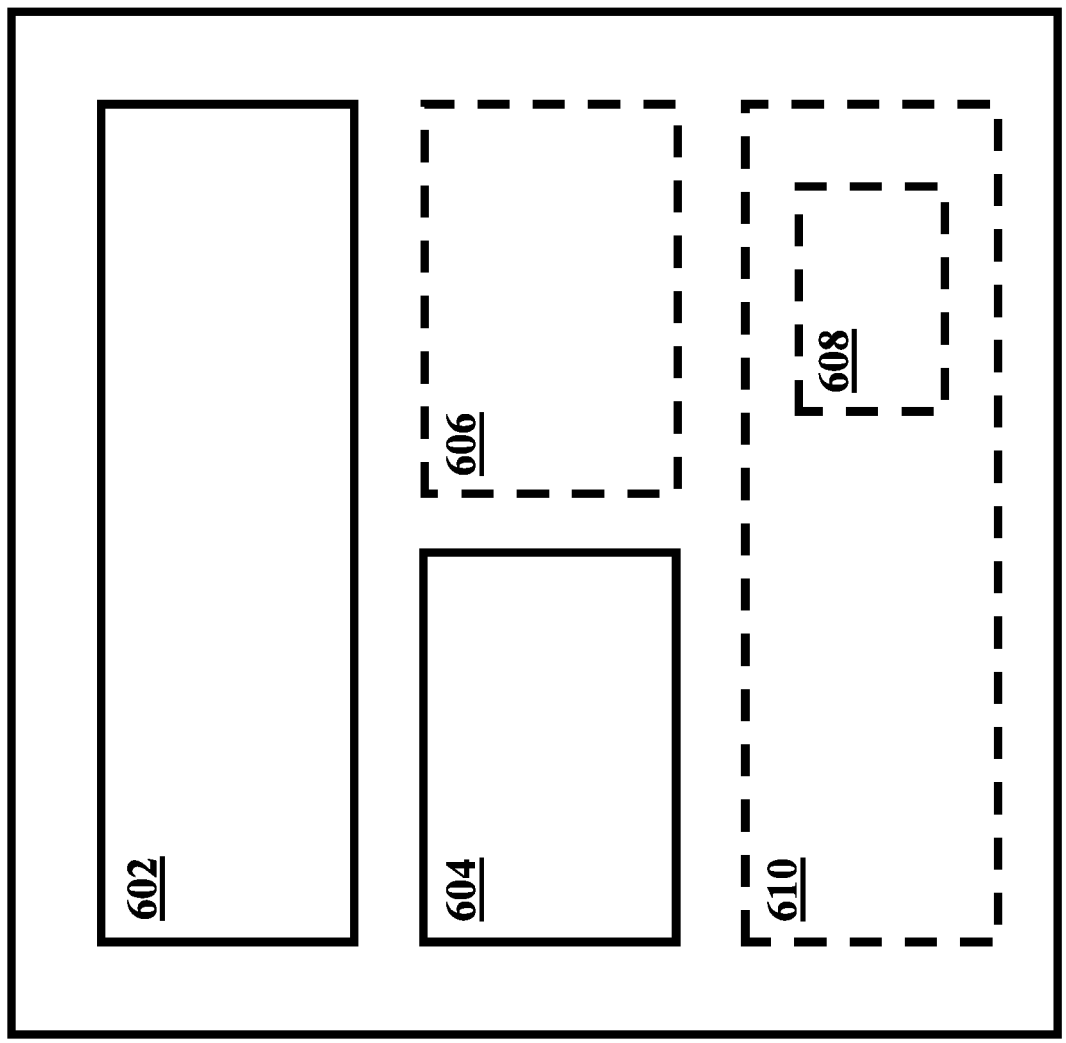
FIG. 6 schematically shows a device for implementing the disclosed method, according to an embodiment of the invention.

FIG. 6 schematically shows a device 600 for implementing the disclosed method, according to an embodiment of the invention.

A device, such as device 600 shown in FIG. 6, may be configured to carry out the aforementioned method. The device 600 comprises a display 602 and one or more processors 604 adapted to execute the steps of the method disclosed herein (i.e. including any optional modification thereto, at least as discussed herein). For example, one or more processors 604 may be adapted to execute the steps of the method 500 shown in FIG. 5.

In some examples, the device 600 may further comprise an imaging device 606 adapted to capture the video capture, as discussed above.

In some examples, the device 600 is a mobile phone having a display 602, processors 604, and a camera (i.e. an imaging device 606). In other examples, the device 600 may be a tablet device, a wearable device, or other such suitable device.

In some further examples, the processors 604 carrying out the method do not form part of the device 600 but are present in some remote environment, e.g. a cloud computing environment; that is, the device 600 may be implemented as a system comprising the device 600. In such examples, the device 600 may be arranged to communicate with the cloud computing environment.

The device 600 may run according to a computer program, such as computer program 608 shown in FIG. 6. The computer program may be stored in a computer readable medium 610 that is stored on the device 600 (as illustrated) or separately thereto. The computer readable medium 610 may optionally be a wave medium or a non-transitory storage medium, according to some examples.

As such, there is disclosed herein a method for displaying quadruped motion metrics, the method comprising: obtaining a video capture of a quadruped comprising at least a video segment spanning a gait cycle of the quadruped; extracting, from the video segment, motion data indicative of lameness of the quadruped; processing the motion data extracted from the video segment to generate a motion metric associated with the video segment; generating a dynamic graphical representation of the motion metric for synchronous display with the video segment; and synchronously displaying the video segment and the dynamic graphical representation of the motion metric on a display.

The invention claimed is:

1. A method for displaying quadruped motion metrics, the method comprising:
   obtaining a video capture of a quadruped comprising at least a video segment spanning a gait cycle of the quadruped;
   extracting, from the video segment, motion data indicative of lameness of the quadruped;
   cropping the video segment to a region of interest, wherein the region of interest comprises at least a portion of the quadruped and the extracted motion data is associated with the portion of the quadruped;

processing the motion data extracted from the video segment to generate a motion metric associated with the video segment;

generating a dynamic graphical representation of the motion metric for synchronous display with the video segment; and synchronously displaying the video segment and the dynamic graphical representation of the motion metric on a display;

wherein the motion data indicative of lameness comprises symmetry data indicative of a gait symmetry, and the motion metric comprises a symmetry metric;

wherein extracting motion data comprises determining a motion of at least two positions on the quadruped captured in the video segment as part of the gait cycle;

wherein determining the motion of the at least two positions comprises determining motion constrained in one dimension; and wherein the at least two positions comprise a head, a thoracoabdominal segment and a pelvis of the quadruped, and the one dimension is a vertical dimension.

2. The method according to claim 1, wherein:
the motion metric is generated for portions of the motion data corresponding to respective portions of the video segment; and synchronously displaying the video segment and the dynamic graphical representation of the motion metric comprises displaying a graphical representation of the motion metric corresponding to a portion of the video segment at a same time as displaying said portion of the video segment.

3. The method according to claim 1, wherein synchronously displaying the video segment and the dynamic graphical representation of the motion metrics on a display comprises at least one of:

displaying the dynamic graphical representation of the motion metric as an overlay over the displayed video capture; and displaying the dynamic graphical representation of the motion metric at a side of the displayed video segment.

4. The method according to claim 1, wherein:
obtaining a video capture of the quadruped comprises obtaining a plurality of video captures of the quadruped, each containing respective video segments spanning at least the gait cycle; and synchronously displaying the video segment and the dynamic graphical representation of the motion metric on the display comprises selecting a video segment from the plurality of video captures for synchronous display with the dynamic graphical representation of the motion metric.

5. The method according to claim 1, wherein:
the video capture spans more than one gait cycle; and
extracting motion data from the video segment comprises segmenting the video capture into at least the video segment spanning the gait cycle.

6. The method according to claim 5, wherein segmenting the video capture comprises:
identifying, from the motion data, a first point in the gait cycle;
identifying, from the motion data, a second point in a subsequent gait cycle, said second point corresponding to said first point; and
segmenting the video capture into a video segment from the first point to the second point.

7. The method according to claim 5, wherein:
the video capture spans a plurality of gait cycles; and
segmenting the video capture comprises segmenting the video capture into multiple video segments, each video segment spanning a respective gait cycle of the quadruped.

8. The method according to claim 7, wherein:
extracting motion data from the video segment comprises selecting the video segment from the multiple video segments of the video capture.

9. The method according to claim 7, wherein:
extracting motion data from the video segment comprises extracting respective sets of motion data for each video segment of the multiple video segments;
generating the motion metric comprises generating the motion metric for each set of motion data;
generating a dynamic graphical representation comprises generating a respective dynamic graphical representation associated with each video segment; and
said synchronous displaying comprises displaying each video segment synchronously with the associated dynamic graphical representation.

10. The method according to claim 7, wherein:
the multiple video segments comprise consecutive video segments from a same video capture.

11. The method according to claim 1, wherein:
at least a portion of the dynamic graphical representation is persisted on the display after displaying the video segment.

12. The method according to claim 11, wherein:
synchronously displaying the video segment with the dynamic graphical representation comprises displaying a dynamic graphical representation associated with a different video segment in addition to the dynamic graphical representation associated with the video segment.

13. The method according to claim 12, wherein:
the dynamic graphical representation associated with the different video segment is graphically represented different to the dynamic graphical representation associated with the video segment.

14. The method according to claim 1, wherein:
the quadruped is a horse.

15. The method according to claim 1, further comprising:
capturing the video capture with an imaging device.

16. The method according to claim 15, wherein:
at least a portion of:
the extracting of the motion data,
the processing of the motion data,
the generating of the dynamic graphical representation, or
the synchronous displaying of the video segment and the dynamic graphical representation of the motion metric,
is performed contemporaneously with said capturing of the video capture.

17. A device comprising:
a display; and
one or more processors adapted to execute the steps of the method of claim 1.

18. The device according to claim 17, further comprising:
an imaging device adapted to capture the video capture, wherein the one or more processors are further adapted to execute the steps of the method of claim 16.

19. A computer program stored in a non-transitory computer-readable medium and comprising instructions to cause the device of claim 17 to execute the steps of the method of claim 1, or to cause the device of claim 18 to execute the steps of the method of claim 15.

20. A non-transitory computer-readable medium having stored therein the computer program of claim 19.

* * * * *